(12) United States Patent
Kasai et al.

(10) Patent No.: US 9,020,849 B2
(45) Date of Patent: Apr. 28, 2015

(54) MRI SYSTEM CENTER AND MRI SYSTEM

(75) Inventors: Yoshimori Kasai, Tochigi (JP); Naoki Sasaki, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 2008 days.

(21) Appl. No.: 11/233,059

(22) Filed: Sep. 23, 2005

(65) Prior Publication Data
US 2006/0020612 A1    Jan. 26, 2006

Related U.S. Application Data

(63) Continuation of application No. 09/959,793, filed as application No. PCT/JP01/01948 on Mar. 13, 2001, now Pat. No. 7,620,662.

(30) Foreign Application Priority Data

Mar. 14, 2000 (JP) .................. 2000-070946

(51) Int. Cl.
*G06Q 10/00*    (2012.01)
*G01R 33/54*    (2006.01)
*G01R 33/28*    (2006.01)
*G06F 19/00*    (2011.01)
*A61B 5/00*    (2006.01)
*G06Q 10/06*    (2012.01)
(Continued)

(52) U.S. Cl.
CPC .............. *G01R 33/546* (2013.01); *G06Q 10/06* (2013.01); *A61B 5/055* (2013.01); *G01R 33/28* (2013.01); *G01R 33/54* (2013.01); *G06F 11/3476* (2013.01); *G06F 19/321* (2013.01); *G06F 19/327* (2013.01); *G06F 19/3418* (2013.01); *A61B 5/0013* (2013.01); *Y10S 707/99931* (2013.01); *Y10S 707/99954* (2013.01)

(58) Field of Classification Search
CPC ....................... G06Q 10/06; G06Q 10/0631
See application file for complete search history.

(56) References Cited

U.S. PATENT DOCUMENTS 5,272,625 A * 12/1993 Nishihara et al. ................ 1/1
5,551,430 A *  9/1996 Blakeley et al. ............ 600/410
5,600,574 A     2/1997 Reitan
(Continued)

FOREIGN PATENT DOCUMENTS

EP        1103902 A2    5/2001
JP        9-168532 A    6/1997
(Continued)

OTHER PUBLICATIONS

Extended European Search Report dated May 23, 2008 in EP 07 02 3597.

(Continued)

*Primary Examiner* — George Chen
(74) *Attorney, Agent, or Firm* — Nixon & Vanderhye P.C.

(57) ABSTRACT

An MRI system center is connected to a plurality of MRI systems for visualizing the interior of a subject to be examined using a magnetic resonance phenomenon, through an electronic communication line. The MRI system center receives data of a log file on which a use state of the MRI systems is recorded or use-state data extracted from the log file, from the MRI systems through a communication control unit. A database unit stores the data of the log file or the use-state data. An analysis unit analyzes the data of the log file or the use-state data received within a given period of time.

6 Claims, 9 Drawing Sheets (51) Int. Cl.
*A61B 5/055* (2006.01)
*G06F 11/34* (2006.01)

(56) References Cited

U.S. PATENT DOCUMENTS

| | | | |
|---|---|---|---|
| 5,740,801 A | | 4/1998 | Branson |
| 5,813,009 A | | 9/1998 | Johnson et al. |
| 5,935,262 A | | 8/1999 | Barrett et al. |
| 5,991,728 A | * | 11/1999 | DeBusk et al. ............... 705/2 |
| 6,282,513 B1 | * | 8/2001 | Strawder .......................... 705/2 |
| 6,331,776 B1 | | 12/2001 | Debbins et al. |
| 6,351,122 B1 | | 2/2002 | Polzin et al. |
| 6,353,445 B1 | | 3/2002 | Babula et al. |
| 6,356,780 B1 | * | 3/2002 | Licato et al. ................. 600/407 |
| 6,381,557 B1 | | 4/2002 | Babula et al. |
| 6,434,572 B2 | * | 8/2002 | Derzay et al. ........................ 1/1 |
| 6,509,914 B1 | | 1/2003 | Babula et al. |
| 6,678,703 B2 | * | 1/2004 | Rothschild et al. ................. 1/1 |
| 6,907,407 B1 | * | 6/2005 | Yamanoue et al. ............. 705/57 |
| 7,620,662 B2 | | 11/2009 | Kassai et al. |
| 2003/0088173 A1 | | 5/2003 | Kassai et al. |

FOREIGN PATENT DOCUMENTS

| | | |
|---|---|---|
| JP | 9-511605 | 11/1997 |
| JP | 9-319451 | 12/1997 |
| JP | 10-78867 | 3/1998 |
| JP | 11-308398 | 11/1999 |
| JP | 11-345322 | 12/1999 |
| JP | 2001-160106 | 6/2001 |
| WO | WO 96/25707 | 8/1996 |

OTHER PUBLICATIONS

Digital Imaging and Communications in Medicine (DICOM), Part 3: Information Object Definitions, [Online] 1999, XP002476578.
Office Action dated Apr. 8, 2008 in JP Patent Application No. 2001-567475 with English translation.
European Patent Office Communication dated May 21, 2007 in Application No. 05007755.1.
Bitti et al., "A WWW-Based Distributed System for Medical Data Analysis and 3D Reconstruction," Jun. 1996, pp. 345-350, XP-002057164.
Official Action mailed on Nov. 2, 2010 in JP 2007-312821 (with English translation).
Healey et al., Adapted waveform encoding for magnetic resonance imaging, Sep.-Oct. 1995, IEEE, vol. 14, 621-638.
Sanders et al., Design and implementation of a clinical MSI workstation, Jun. 14-17, 1992, IEEE, 138-146.
Notice of Allowance and Fee(s) Due mailed Jul. 17, 2009 in U.S. Appl. No. 09/959,793.
Office Action mailed Dec. 24, 2008 in U.S. Appl. No. 09/959,793.
Office Action mailed Jul. 27, 2007 in U.S. Appl. No. 09/959,793.
Interview Summary mailed May 18, 2007 in U.S. Appl. No. 09/959,793.
Office Action mailed Dec. 28, 2006 in U.S. Appl. No. 09/959,793.
Office Action mailed Apr. 6, 2006 in U.S. Appl. No. 09/959,793.
Office Action mailed Dec. 19, 2005 in U.S. Appl. No. 09/959,793.
Office Action mailed Mar. 25, 2005 in U.S. Appl. No. 09/959,793.

* cited by examiner

MRI SYSTEM CENTER AND MRI SYSTEM

CROSS-REFERENCE TO RELATED APPLICATIONS

This is a continuation/division of our earlier application 09/959,793 filed Nov. 7, 2001 now U.S. Pat. No. 7,620,662 which is, in turn, a Continuation Application of PCT Application No. PCT/JP01/01948, filed Mar. 13, 2001, which was not published under PCT Article 21(2) in English.

This application is based upon and claims the benefit of priority from the prior Japanese Patent Application No. 2000-070946, filed Mar. 14, 2000, the entire contents of which are incorporated herein by reference.

BACKGROUND OF THE INVENTION

1. Field of the Invention

The present invention relates to an MRI system for visualizing the interior of a subject to be examined using a magnetic resonance phenomenon and an MRI system center.

2. Description of the Related Art

Magnetic resonance imaging (MRI) is widely used as a method for acquiring, for example, an anatomical cross-sectional view of a human body in a noninvasive manner. The MRI allows an image having various contrasts to be acquired in accordance with variations in imaging conditions such as repetition time TR and echo time TE.

Recently, the improvement of pulse sequence has made it possible to generate an image containing functional information such as diffusion and reflux. Since these imaging steps include a step of visualizing blood vessels using MRA (magnetic resonance angiography), they can be combined to carry out an appropriate diagnosis, making their clinical value extremely great.

Pulse sequences are improving from day to day, and more useful imaging conditions and imaging procedures are produced and reported from the user side one after another. In the present exemplary embodiment, these imaging conditions and imaging procedures produced chiefly from the user side are referred to as clinical protocols.

On the other hand, there are not a few pulse sequences in which the number of imaging condition items that can freely be changed on the user side is increased several times as compared with that of several-year-old items in accordance with the maturity of MRI. As the types of pulse sequences increase, the possible variations of imaging procedures widen.

However, a great deal of expertise is needed to set the imaging conditions and imaging procedures. Thus, one who can constitute a very useful clinical protocol by effective use of a set range of the imaging conditions and imaging procedures will be limited to a very small number of doctors or technicians.

Under the present circumstances, therefore, a useful clinical protocol may neither spread nor be promoted at all.

The problem of a delay in spread or promotion is not limited to the clinical protocol. Even though a new, useful pulse sequence or application is developed, its spread sometimes makes very slow progress. Usually the sales staff makes their rounds of facilities and hospitals in order to try to put such a pulse sequence and application into widespread use. However, it takes time to make the rounds, and most pulse sequences and applications are already on sale as package software. Hospitals often hesitate to purchase such package software because it is expensive.

BRIEF SUMMARY OF THE INVENTION

An object of the present invention is to spread and promote hardware, applications, pulse sequences, and clinical protocols in MRI.

An MRI system center is connected to a plurality of MRI systems for visualizing an interior of a subject to be examined using a magnetic resonance phenomenon, through an electronic communication line. The MRI system center receives data of a log file on which a use state of the MRI systems is recorded or use-state data extracted from the log file, from the MRI systems through a communication control unit. A database unit stores the data of the log file or the use-state data. An analysis unit analyzes the data of the log file or the use-state data received within a given period of time.

DETAILED DESCRIPTION

A preferred embodiment of the present invention will now be described with reference to the drawings.

Figure 1:
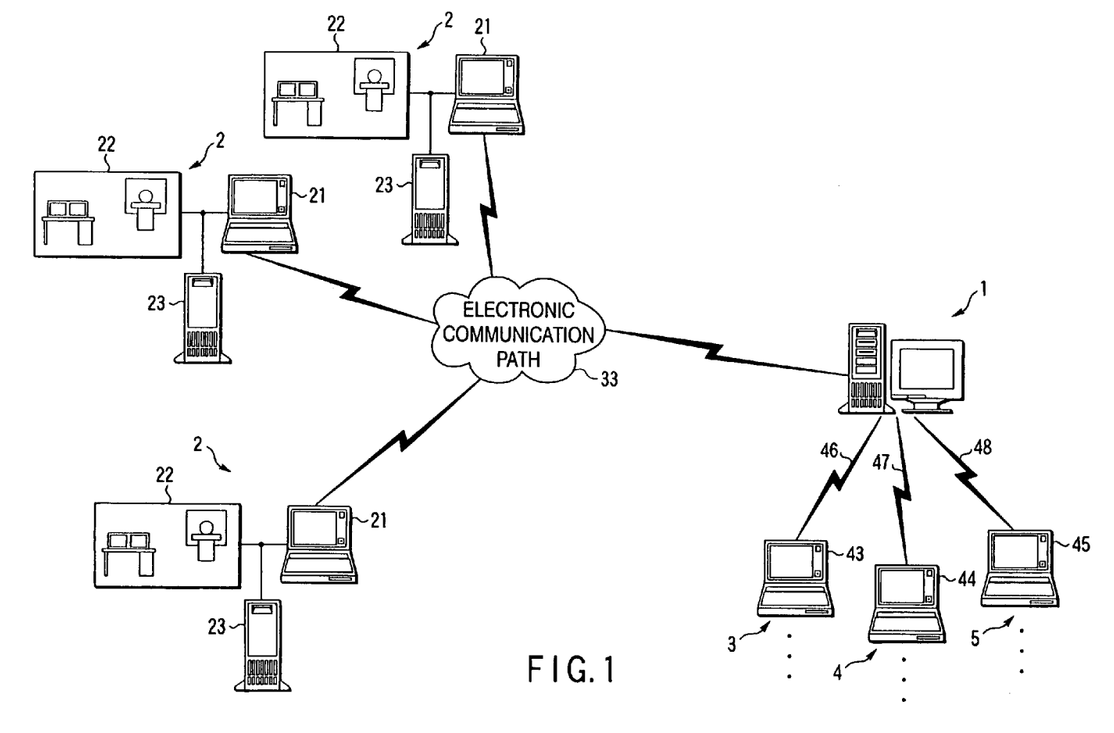
FIG. 1 is a block diagram of the whole of a system according to an embodiment of the present invention, including an MRI system center as the center thereof.

FIG. 1 shows the whole configuration of a system according to the present embodiment. A plurality of MRI systems 2, which are installed in their respective hospitals, are each connected to an MRI system center 1 through a private line or an electronic communication path 33 such as a public line. Each of the MRI systems 2 includes an MRI device 22, a communication terminal (hospital terminal) 21, and a storage device 23.

A plurality of sales division systems 3, which are installed in sales divisions or sales companies for selling MRI devices and their consumable items, are each connected to the MRI system center 1 via a private communication path 46. Each of the sales division systems 3 includes a communication terminal (sales terminal) 43.

A plurality of maintenance service division systems 4, which are installed in maintenance service divisions or maintenance service companies for maintaining the existing MRI devices, are each connected to the MRI system center 1 via a private communication path 47. Each of the maintenance service division systems 4 includes a communication terminal (maintenance service terminal) 44.

A plurality of development division systems 5, which are installed in development divisions or development companies for designing and developing MRI devices and their constituting elements (parts) such as RF coils and for developing pulse sequences, image processing applications and the like, are each connected to the MRI system center 1 via a private communication path 48. Each of the development division systems 5 includes a communication terminal (development terminal) 45.

Figure 2:
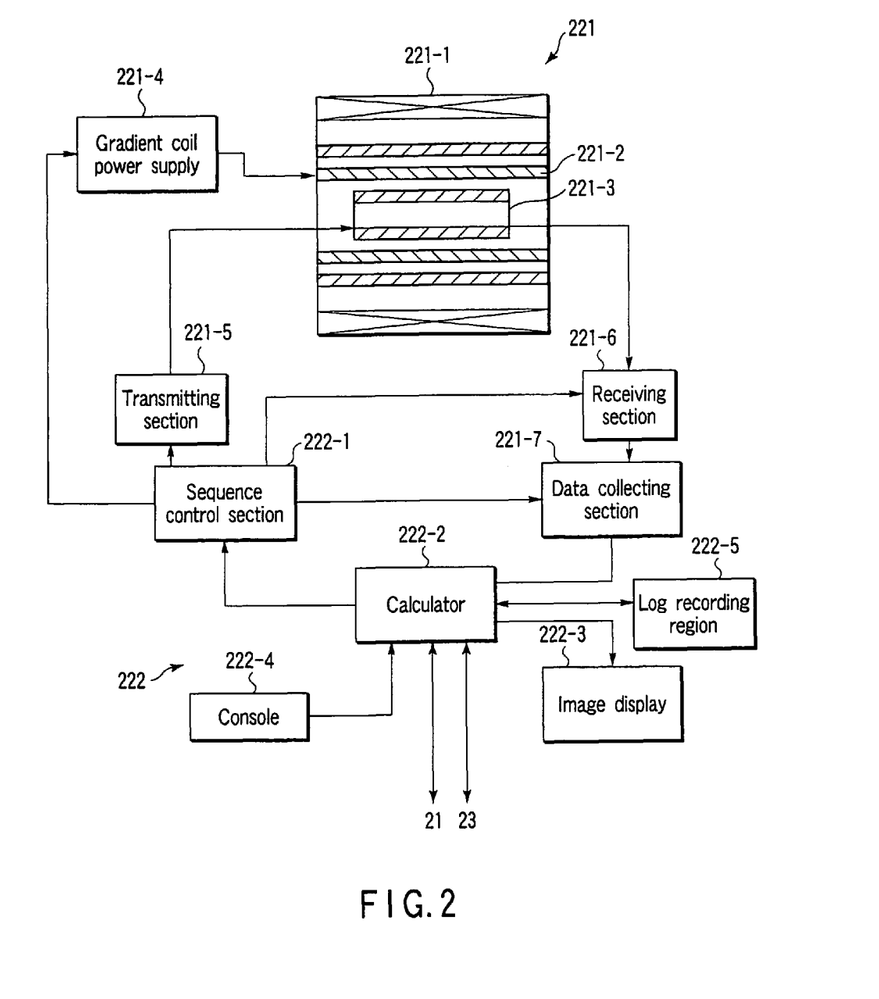
FIG. 2 is a block diagram of the MRI system shown in FIG. 1.

FIG. 2 illustrates a configuration of the MRI device 22. The MRI device 22 includes a gantry 221 and a computer unit 222. The gantry 221 has a magneto-static field magnet 221-1, a gradient magnetic field coil 221-2 for generating a gradient magnetic field pulse upon receiving a current from a gradient coil power supply 221-4, and a radio-frequency coil (RF coil) 221-3 for generating a radio-frequency magnetic field and detecting a magnetic resonance signal. The radio-frequency coil 221-3 can serve as both a transmitter and a receiver or include a transmission coil and a reception coil separately from each other. As is known, the radio-frequency coil 221-3 is an essential constituting element for determining a sensitivity region, sensitivity uniformity, and an S/N ratio of MRI. Since there is a trade-off relationship between the area of the sensitivity region and the S/N ratio, it is common to selectively use the optimum RF coil in respective portions.

When the radio-frequency coil 221-3 transmits a radio-frequency magnetic field, a transmitting section 221-5 is connected to the coil 221-3. When the radio-frequency coil 221-3 receives an MR signal, a receiving section 221-6 is connected to the coil 221-3. The gradient coil power supply 222-1, transmitting section 222-2, and receiving section 222-3 generate a radio-frequency magnetic field pulse in accordance with a desired pulse sequence under the control of a sequencer 222-1 and then a gradient magnetic field pulse, and receive an MR signal.

The MR signal, which is amplified, detected and digitized in the receiving section 221-5, is sent to a calculator 222-2 through a data collecting section 221-7. The calculator 222-2 reconstructs image data in response to the MR signal. The image data is displayed on an image display 222-2. A console 222-4 is connected to the calculator 222-2. An operator operates the console 222-4 to input all instructions regarding the operations of the MRI device such as selection of clinical protocols, that of pulse sequences, and setting of imaging conditions. The communicating computer 21 and storage device 23 are connected to the calculator 222-2. These units need not always be provided in the same facilities. If the units have the same function even though they are located geographically away from each other, they can be included in the system center of the present invention.

Figure 3:
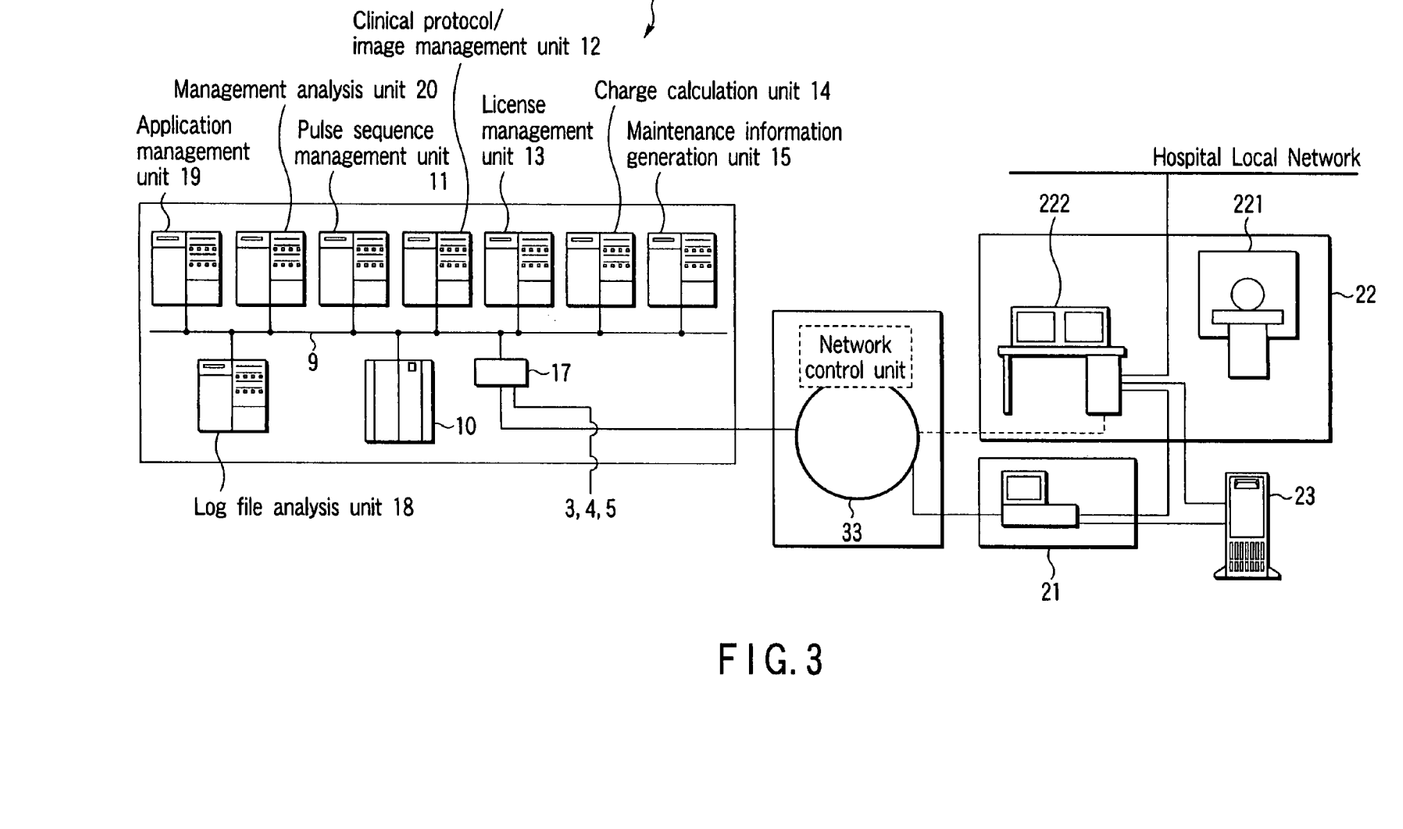
FIG. 3 is a block diagram of the MRI system center shown in FIG. 1.

FIG. 3 illustrates a configuration of the system center 1. The system center 1 is connected to a circuit 3 via a communication control device 17. The communication control device 17 is connected to a control/data bus 9. A database unit 10, a pulse sequence management unit 11, a clinical protocol/image management unit 12, a license management unit 13, a charge calculation unit 14, a maintenance information generation unit 15, a log file analysis unit 18, an application management unit 19, and a business analysis unit 20 are connected to the bus 9.

Figure 4:
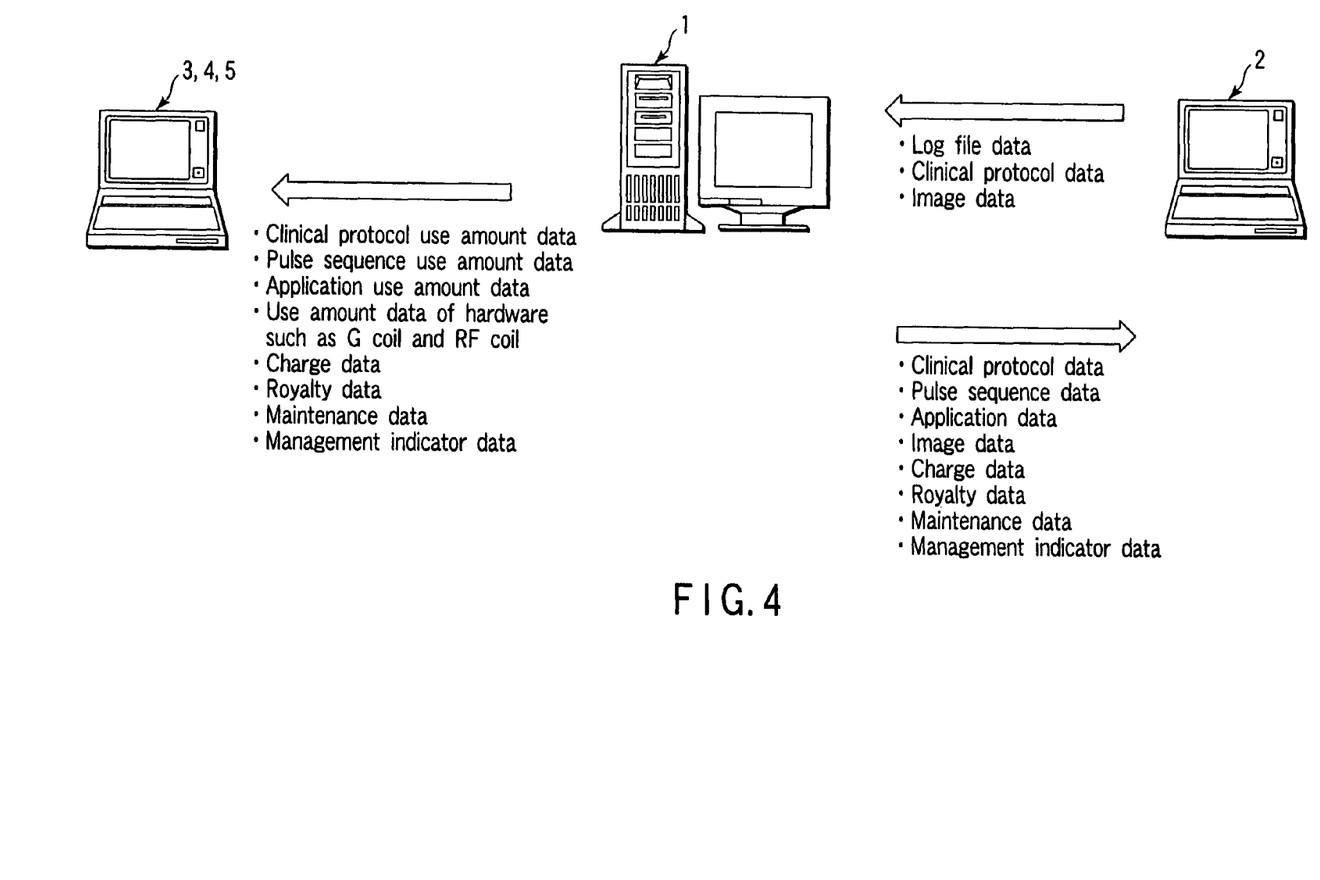
FIG. 4 is a view showing data communicating between the MRI system center of FIG. 1, a hospital terminal, and a sales division terminal (maintenance division terminal, development division terminal).
Figure 5:
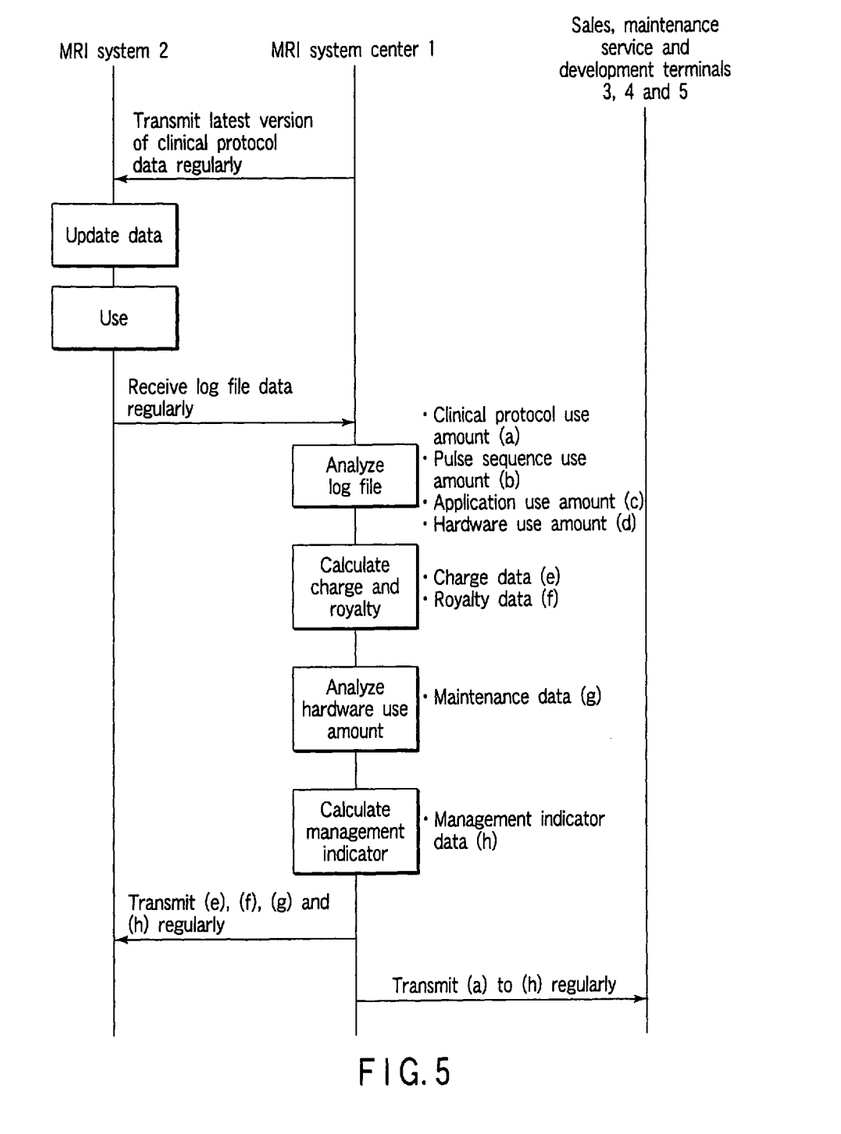
FIG. 5 is a view showing communication procedures between the MRI system center of FIG. 1, a hospital terminal, and a sales division terminal (maintenance division terminal, development division terminal).

FIGS. 4 and 5 are illustrations of an operation of the present embodiment. The database 10 of the MRI system center 1 stores data of a plurality of pulse sequences, data of a plurality of applications used for image processing and the like, data of a plurality of clinical protocols, and data of a plurality of images.

These data items are updated at any time and the latest ones are always stored in the database 10. The latest data items are periodically transmitted to the MRI system 2. The MRI system 2 receives the transmitted data items through the hospital terminal 21 and updates data of the storage device 23. Thus, the storage device 23 stores data of a plurality of pulse sequences, data of a plurality of applications used for image processing and the like, data of a plurality of clinical protocols, and data of a plurality of images, which are the same as those of the database 10. In the MRI system 2, the latest pulse sequence, application (install program), and clinical protocol can always be used, and the latest image data can always be referred to.

The system center 1 periodically receives log file data from the MRI system 2.

Log files are created by various types of software such as a sequence, image reconstruction, and a scan queue manager in the calculator 222-2 of the MRI system 2, and then recorded temporarily in a log-recording region 222-5. The log files are generally unorganized history files on which all states of the operation of the MRI system 2 are recorded. If the log files are organized, most of them are occupied by use-state data. Instead of sending log file data to the system center 1 from the log-recording region 222-5 of the MRI system 2, the log file included in the log-recording region 222-5 can be analyzed by the calculator 222-2 of the MRI system 2 to extract use-state data and transmit the use-state data to the MRI system center 1. This embodiment will be explained on condition that the log file data is transmitted.

The log files are recorded including not only the use state of hardware such as RF coils constituting the MRI device 22, but also that of software such as pulse sequences, applications, clinical protocols and image data. More specifically, the log files include the type of the used pulse sequence, the number of times of use of the pulse sequence, the number of exposures, the number of output films, the type of the used RF coil, the number of times of use of the RF coil, the use time of an RF amplifier, an average power of a gradient magnetic field amplifier, the intensity of a gradient magnetic field, the number of times of use of a clinical protocol, the type of the used application, and the number of times of use of the application.

The clinical protocols chiefly include practical information concerning imaging conditions and imaging procedures. In other words, the clinical protocols are clinically useful information about imaging conditions and imaging procedures that doctors or photographers would discover by trial and error. This information includes the type of RF coils, filming, a combination of pulse sequences, repetition time TR and echo time TE of pulse sequences, the amount of RF irradiation (SAR) absorbed by a subject to be examined, the number of slices, the size of the used matrix, and various parameters (imaging conditions) in a pulse sequence, such as resolution.

As described above, the software (i.e., computer programs) such as pulse sequences, applications, clinical protocols and image data is stored in the storage device 23. When an operator gives an instruction to the calculator 222-1 to gain access to his or her desired data, its access record (access time, access number, etc.) is recorded in a log file as a use state of the software.

The database 10 of the MRI system center 1 stores log file data that is received from all the MRI systems 2 connected to the database 10 via the circuit 33 and making a given contract therewith. The log file analysis unit 18 analyzes log file data of a given time period (e.g., one month) stored in the database 10 to compile both the amount of use (the number of times of use, the use time, etc.) of software such as pulse sequences, applications, clinical protocols, and image data within a given time period and the amount of use (the number of times of use, the use time, etc.) of hardware such as RF coils for each of the MRI systems 2. The log file analysis unit 18 includes programs for conducting an analysis according to various purposes, which will be described later, and transmits an analysis result to the development division system 5.

The pulse sequence management unit 11 performs management operations for newly registering pulse sequence data, which is supplied chiefly from the maker side, in the database unit 10, updating the data therein, and deleting it therefrom. The application management unit 19 performs management operations for newly registering an application, which is supplied from the maker side, in the database unit 10, updating the application therein, and deleting it therefrom.

The clinical protocol/image management unit 12 performs management operations for newly registering image data and clinical protocol data, which are generated from the user side (MRI system 2), in the database unit 10, updating the data therein, and deleting it therefrom. The license management unit 13 imposes a limitation on the hierarchy of data transmitted to the storage device 23 or that of access to the database unit 10 based on individual information (user ID) sent from the MRI systems 2.

The charge calculation unit 14 calculates a charge for use for each of the MRI systems 2 based on data of the amount of use of hardware and software analyzed by the log file analysis unit 18 and the unit charge for the use time or the number of times of use of each of hardware and software. The unit 14 also calculates a royalty for a provider of clinical protocol data and image data uploaded with a license from each of the MRI systems 2.

The maintenance-supported unit 15 estimates information for supporting maintenance service of the MRI systems 2, such as a schedule of maintenance service and a cause of malfunction, based on the analyzed use-amount data of hardware. In case of malfunction, the unit 15 can estimate a cause of the malfunction from the use-state data of a log file. In the currently used MRI device, its malfunction seldom exercises an influence upon all pulse sequences or images, and an image artifact is generated from a combination of specific conditions. The use of the above log file allows the cause of malfunction to be found from images. The maintenance-supported unit 15 estimates the cause of malfunction from the log file.

The business analysis unit 20 generates various types of management indicator data from the use-amount data of hardware and software, which is analyzed by the log file analysis unit 18. The management indicator data is, for example, the number of patients a day and the time required for photography that are useful for running a hospital.

The above charge data, royalty data, maintenance data, and management indicator data as well as software data such as clinical protocols are transmitted to the MRI systems 2 of hospitals from the MRI system center 1.

Clinical protocol use-amount data, pulse sequence sequence use-amount data, application use-amount data, use-amount data of hardware such as RF coils, charge data, royalty data, maintenance-supported data, and management indicator data are transmitted from the MRI system center 1 to a sales division terminal 3, a maintenance service division terminal 4, and a development division terminal 5. The sales division, maintenance service division, and development division are capable of using the transmitted data for planning a sales strategy, drawing up a maintenance schedule, planning a development policy, and the like.

The above mechanism brings about various advantages to both the maker side and the user side. The maker side (system center side) can promote the spread of pulse sequences, applications, clinical protocols, etc. Since, moreover, the maker side analyzes a log file (use-state data) to obtain an amount of use statistically, they can adopt a sales strategy and make a development program so as to meet their needs. They can also offer maintenance service at appropriate times.

The user side (MRI system side) can always use the up-to-date pulse sequence, application, clinical protocol and image. Unlike in the prior art, the user need not pay the costs at once to update a pulse sequence and an application in accordance with the provision of a package from the maker, and he or she is charged on an as-used basis. The standard for passing the charge to a patient is thus clarified. In other words, if the user uses the log file described above, he or she can measure the amount of use for each pulse sequence; therefore, he or she has only to pay the maker for the amount of use. At present, there are approximately 100 to 200 pulse sequences. If the user purchases all of them, he or she has to bear the costs corresponding thereto. If the user selects payment according to the amount of use, he or she can purchase software as not initial costs but running costs.

Since a considerable royalty can be paid for the provision of clinical protocols and images that are devised in a variety of ways in accordance with a case of each user side, the clinical protocols and images can be spread and promoted. Needless to say, not only the clinical protocols and images but also new pulse sequences and applications can be updated from the MRI system 2 to the database unit 10 of the center 1.

A charge for the amount of use of a pulse sequence from the maker to the user is calculated and so is a charge for both the amount of use of a pulse sequence from the user to the patient and the occupied time (photographing time) of the MRI device, which clarifies the mechanism for causing the costs. This clarification is useful for releasing a new pulse sequence. For example, the following sales activity can easily be carried out. A salesperson provides binary software distributed via a network and a license used free within a limited time period, determines image quality and clinical effectiveness, and recommends purchasing the license permanently. The sales activity thus requires a mechanism for issuing the license.

Figure 6:
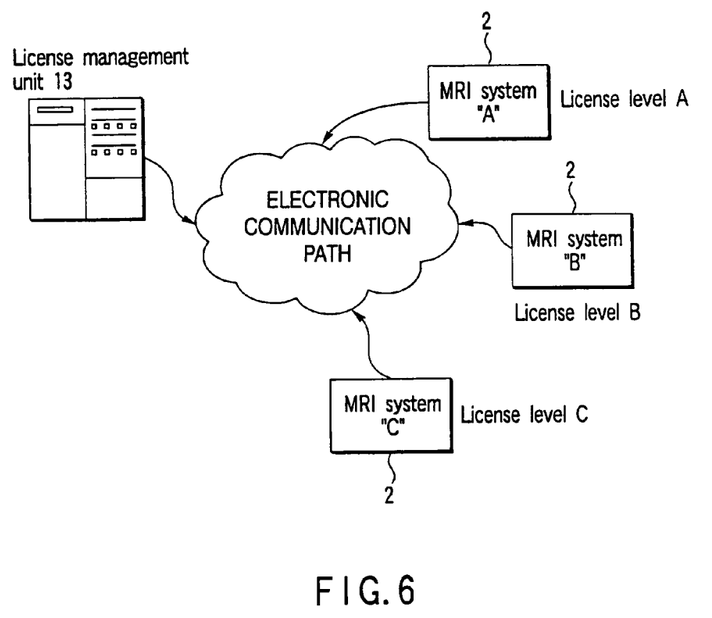
FIG. 6 is a conceptual diagram of license management performed by a license management unit shown in FIG. 2.

By associating an access level with software of clinical protocols, image data, etc., the license management unit 13 can impose a limitation on the range of provision, as shown in FIG. 6, in accordance with the level of a license (access authority) that is contracted with a user. However, the provision of the clinical protocols and image data to the system center 1 is directed to all users and thus basically there is no difference among them.

License level C: only browsing of images
License level B: images+simplified clinical protocols
License level A: images+detailed clinical protocols With the above access authority, a limitation is imposed on information to be provided. The maker can receive a royalty as not money but the right to use the clinical protocols and sequences. The maker can perform an appropriate evaluation of user's information and pay a royalty in terms of the right to use the clinical protocols and sequences.

The charges that the user pays when he or she contracts are set so as to vary with a difference in license level. Furthermore, the programs of the license management unit 13 can be set such that the license level is upgraded at no charge for a user who provides a clinical protocol when the frequency of use of the clinical protocol measured in the log file analysis unit 18 is not lower than a fixed one. In this case, the system center 1 transmits a notification that the license level has been changed to the MRI system 2. Not only the frequency of use of clinical protocols but also the other contributions such as a scientific contribution can be counted as points and input to the system center 1.

The advantages of the present embodiment will be explained in detail hereinafter.

1-1 [Spread and Promotion of Clinical Protocols]

The foregoing clinical protocols represent an imaging procedure and include pulse sequences and their specific parameters such as TR and TE. However, it can be considered that information of know-how about selection of resolution, that of contrast and the like according to an RF coil and an imaging portion rather than the parameters themselves includes an important value. In other words, it is principally a clinical protocol that is devised for each facility, and a great benefit arises from the spread and expansion of the clinical protocol for the very same reason as that in the pulse sequences.

Since, however, the legibility of clinical protocols is great, they are harder to protect than the pulse sequences (they can easily be imitated with little influence on image quality if there is a slight change in TR or the like). Thus, a mechanism similar to the protection of copyright is needed. In other words, it is difficult to protect the clinical protocols singly, so that a log file is created based on access to the storage device 23 in which the clinical protocols are stored or access to the database 10 of the center 1. Consequently, the use state of clinical protocols can correctly be measured like the amount of use of pulse sequences and applications.

There may be a case where some facilities do not wish to provide any clinical protocols to the outside. The range of provision can thus be controlled by changing the setting of a level at which the state of use is extracted from the log file.

The adoption of the above mechanism allows an effective clinical protocol developed in each facility to be registered in the center 1 with a licensing agreement and used in other facilities. The following methods for paying a royalty to a user who has provided an effective clinical protocol can be considered:

1) The maker side purchases the effective clinical protocol and sells it to another facility.

2) The royalty is settled between facilities but not through the maker.

3) The royalty is canceled out by new pulse sequence data and applications provided at no charge from the maker side.

In any case, it is considered that an effective clinical protocol is spread and promoted by a combination of provision, royalty and control. Since both charge and royalty are caused due to use, information is not provided only in one direction from the maker side, but the contribution of information such as know-how called a clinical protocol, which requires a high degree of medical knowledge, can be quantified from a clinical standpoint; consequently, the information can be shared and the royalty can be set, and the clinical protocol can easily be introduced into other facilities.

As described above, the useful clinical protocols and image data often occur on the user side. It is thought that its spread is promoted while being supported by both charge and royalty.

Figure 7:
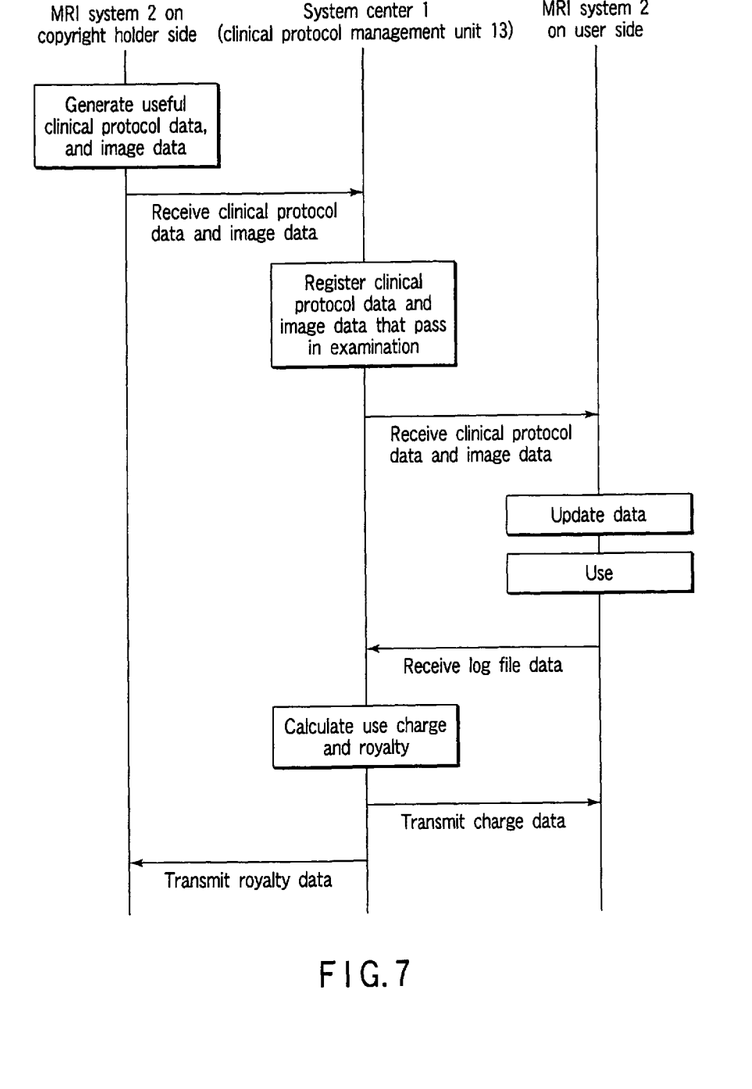
FIG. 7 is a chart showing a store and forward procedure of clinical protocols in the present embodiment.

FIG. 7 shows a procedure for spreading a clinical protocol and image data. When a clinical protocol or an image, which is considered to be useful according to doctor's or photographer's own judgment, occurs in the MRI system 2 of a certain hospital, the useful clinical protocol or image data is transmitted to the center 1 from the MRI system 2. In the center 1, the usefulness of the clinical protocol or image data is examined and if it passes in the examination, it is registered in the database 10 and transmitted to the MRI system 2.

In the MRI system 2, the transmitted clinical protocol or image data is stored in the storage device 23, and old data is deleted (updated) when the need arises.

When the clinical protocol or image data is used in the MRI system 2 of a certain hospital, its use state is sent to the center 1 as a log file or use-state data. The charge calculation unit 14 of the center 1 calculates a use charge of a user in accordance with his or her use state (amount of use) and also calculates a royalty of an information provider (copyright holder). Then, charge data and royalty data are periodically transmitted to their respective MRI systems 2 of the user and the information provider. The user is supplied with a bill according to one of an on-line payment method and an off-line payment method that the user chose when he or she contracted with the provider. When the user does not pay by the due date, the center 1 gives a warning to the MRI system 2; nevertheless, when the user does not pay yet within a fixed period of time, it is possible to take measures, e.g., to rewrite the programs in the MRI system 2 to inhibit the clinical protocol from being used.

Furthermore, the clinical protocol or image data need not be transmitted from the center 1 to the MRI system automatically, but the user can access the center 1 to download a necessary clinical protocol therefrom.

Figure 8:
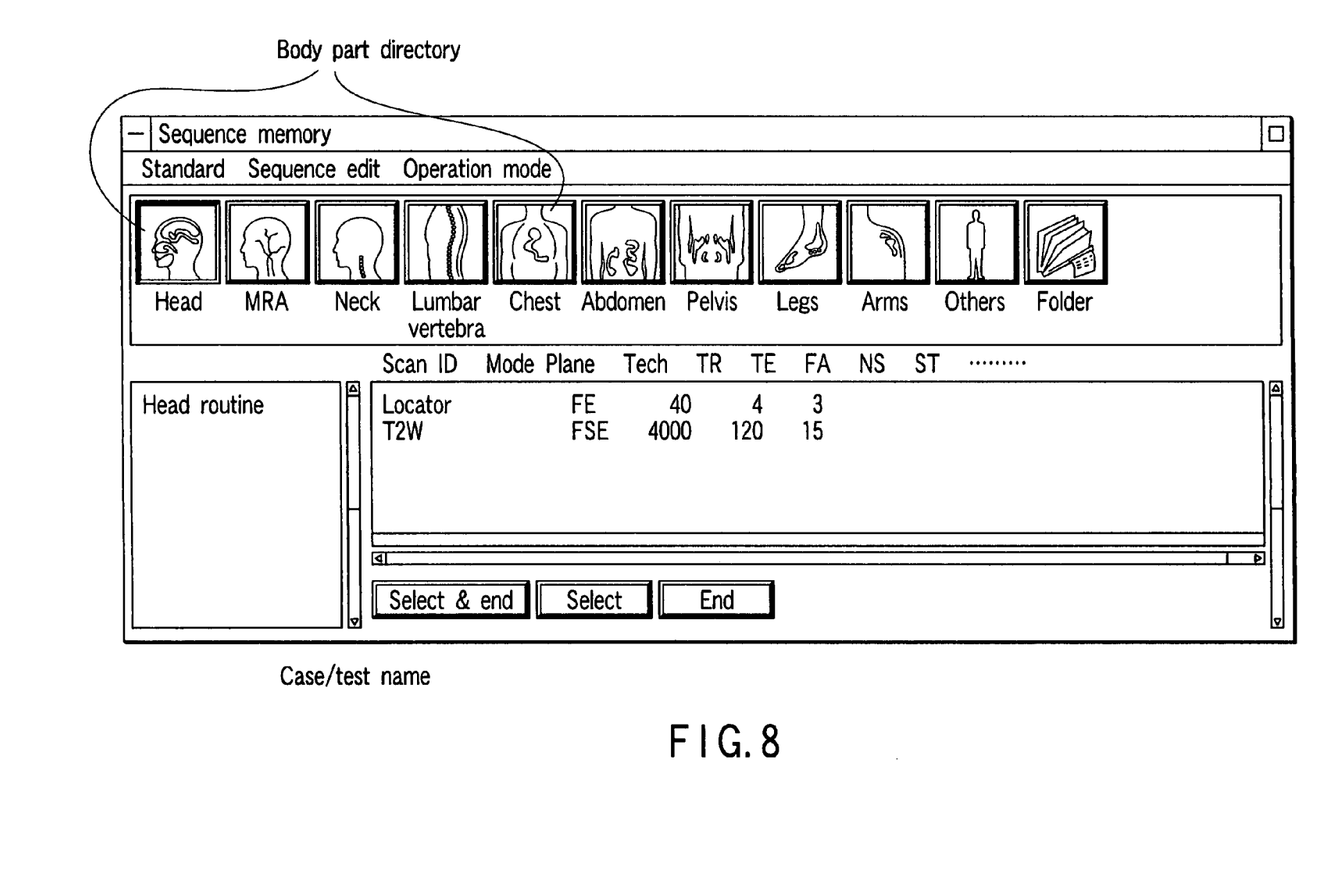
FIG. 8 is a view of select screens of clinical protocols displayed on a display of the MRI system in the present embodiment.

FIG. 8 illustrates a main screen for selecting a clinical protocol. A plurality of body part directory buttons are displayed on the screen. A picture indicating each body part is drawn on its corresponding button. An imaging procedure option corresponding to a selected body part directory is displayed on the left side of the screen. Only one type option called a head routine is displayed on the screen shown in FIG. 8. Simple information of a selected imaging procedure option is displayed on the right side of the imaging procedure option. On the screen of FIG. 8, a locator is used to locate an imaging position by a field echo (FE) method, and the position is displayed in terms of specific values of recommended imaging conditions (TR, TE, NS) of a pulse sequence. A doctor or photographer can determine a clinical protocol for use with reference to the imaging procedures and imaging conditions.

Figure 9:
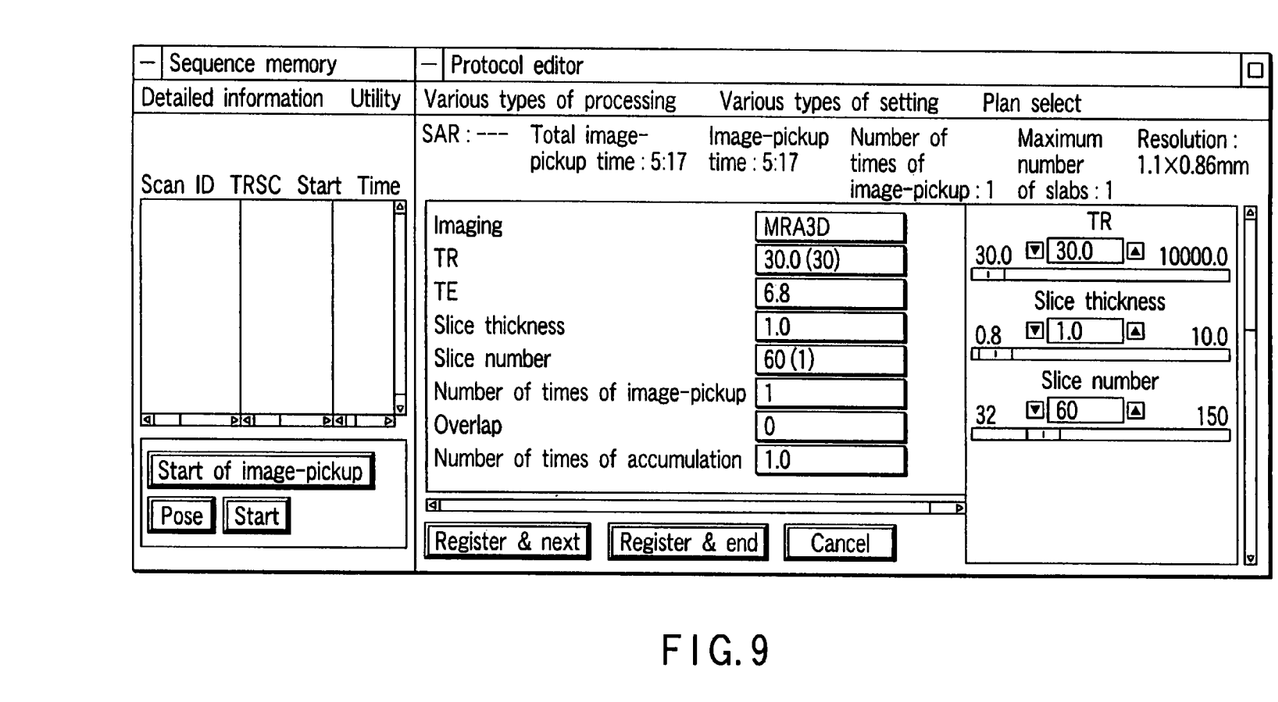
FIG. 9 is a view of editing screens of clinical protocols displayed on the display of the MRI system in the present embodiment.

When the user depresses a select end button, a clinical protocol for use is determined and its corresponding clinical protocol data is loaded into the calculator 222-2 from the storage device 23. Concurrently, a protocol editor is started and, as shown in FIG. 9, an edit screen of imaging conditions is displayed. The user can freely change a value of the imaging conditions on the screen.

As described above, the select and edit screens are so configured that a clinical protocol can be selected and edited very simply.

In the foregoing description, software data is stored in the storage device 23 on the user side, and the storage device 23 is accessed from the MRI device 22. However, various showcases can be prepared on a WWW server as operating patterns of the center 1 on the maker side, and the respective features of a new pulse sequence and application and the images obtained can be browsed. Information of only the outline of imaging conditions and sequences for use can be provided as a clinical protocol and in particular a clinical image and a case can be browsed. The user can browse a clinical protocol by the Internet browser or the like and download his or her favorite one for trial. In this case, a program that can be used free for the first fixed period of time or the fixed number of times is incorporated into software and then the user catalogues it formally, with the result that the program is charged based on usage track records. As in trial software of PC and the like, the limiting conditions such as resolution, the number of slices, and the function of printing on a film can be set. As for clinical protocols, a downloaded one is modified and utilized in accordance with the actual conditions of facilities. When a clinical protocol is improved, it is uploaded to the center 1 to share information. If a service such as exemption of the amount of use of the original clinical protocol is provided according to an extent of improvement, the protocol can be activated.

1-2 [Charging Function]

As described above, it is possible to charge for the amount of use of clinical protocols as well as the use of pulse sequence data and applications provided by the maker. In other words, a log file can count the use of a clinical protocol and its download. Since a clinical protocol that is created from not the maker side but the user side (clinical site) is very useful, the copyright on the clinical protocol belongs to the user in most cases. If, however, the use charge of a charging system is collected on a fixed-charge basis or at a fixed rate for the amount of use of clinical protocols, the clinical protocol charging system can be maintained within a rational range.

1-3 [Aggregation of Clinical Protocol Data via Network]

If the center 1 periodically accesses the database unit 10 of the use state of clinical protocols or the user positively uploads a clinical protocol, clinical protocol data can be aggregated in the center 1. The following service can be provided using the clinical protocol data.

[Search for Sequence Usage Rate via Network]

If the amount of use of each sequence is measured in time sequence and a result of the measurement is transmitted to the development division system 5, the maker side can know which sequence is used frequently. If data of the usage conditions of sequences is collected and supplied to the development division system 5, the maker side can analyze the usage conditions of a sequence used frequently and collect information based on which it is determined whether the clinical effectiveness can efficiently been enhanced if which part of the sequence is improved.

1-4 [Maintenance of Clinical Protocol Database Unit for Browsing]

Image data and clinical protocol data are configured as a database that can be publicly opened, and a difference in access authority of database unit 10 is caused in the license management unit 13 as illustrated in FIG. 6. However, the upload is directed to all users and thus basically there is no difference between them.

License level C: only browsing of images+types of images
License level B: images+simplified clinical protocols
License level A: images+detailed clinical protocols The presence and absence of the above access authority causes a difference in information to be provided. The maker provides information for the user who has paid a royalty in terms of information or money. The maker performs an appropriate evaluation of user's information such as a clinical protocol and pays a royalty in terms of the right to use the clinical protocols and sequences.

1-5 [Use of Clinical Protocol Database Unit]

Case data similar to that stored in the database unit 10 is accessed from the development division system 5, and the clinical protocols corresponding to the data are compared with one another. The maker side proposes a clinical protocol that is considered to be more effective to the user.

1-6 [Means for Catching Variations in Trend of Clinical Protocols]

In addition to the maker-side convenience of allowing development that fills the user needs by monitoring variations in the way to use a sequence from the amount of use of pulse sequences of all users and the parameters for use, the clinical protocols can be applied to an investigation of clinical trends by health insurance and a government body.

1-7 [Proposal of Deviation of Amount of Use of Clinical Protocol from Model Case]

The maker side can grasp a model case regarding the optimum method of use for each MRI system 2 by the output data representing a trend of each sequence. Thus, the maker side can propose an improvement of a sequence and a clinical protocol the amount of use of which is large, or present a model thereof to the user.

2 [Provision of Management-Supported Information]

The center 1 can create a report on the support of hospital management or the like, which contains statistical data such as a variation of the entire site from an average, performance a day, use time for each patient, and a variation in the way of use of a sequence, and the MRI system 2 can output the report. The maker side can propose an improved one of a pulse sequence to the user according to the amount of use based on the statistical data.

3 [Network+Charges]

Information of the amount of use of clinical protocols, sequences and applications can be collected via a network and charged according to the amount of use.

If the user states of MRI devices are counted more closely in consideration of the above, the sales do not rely on a conventional system in which hardware is purchased from a wholesaler without the right to return it, but a hardware-based service is continuously provided, with the result that both the maker and user can make a profit. The pulse sequence by which a fund can be raised is provided free, and the user can direct his or her study to a pulse sequence whose development will be required or whose effectiveness is high.

4-1 [Example 1 of Use of Log File (Amount of Use of RF Coil)]

A user of the MRI system 2 mounts the RF coil 221-3 on a subject to be examined when he or she uses the MRI system 2. The MRI system 2 is capable of knowing what RF coil 221-3 is mounted by an automatic electrical means or by operator's hand. The computer 222 for controlling the MRI system 2 is therefore capable of knowing how much the RF coil 221-3 is used a day for each RF coil 221-3.

The computer 222 delivers use-state data of the RF coil 221-3 to the computer 21 for communicating a log file in specific time units (real time, one day, one week, etc.).

The communicating computer 21 changes the delivered data to an appropriate time unit (real time→one day, one day→one week, etc.) or delivers it to the center 1 without being changed. The results delivered to the center 1 are sorted for each installation site of the MRI system 2 or according to attribute information such as the number of beds in a hospital, specialization areas, sales/service areas, sequences, and target portions and processed statistically and then presented to the development division system 5. The amount of use of RF coil can thus be detected for each attribute.

The above result allows a profit to be provided for both one who conducts an analysis and a user of the MRI system in a sense that it can be provided for the following judgments.

(1) The service lifetime of an RF coil can be controlled for a user who uses a specific RF coil with a high frequency and the quality of diagnosis can be maintained.

When the expiration date of the RF coil is imminent, the center 1 transmits its notification to the user of the maker side. Based on the notification, the user is able to make a choice among repair, replacement and the like before the RF coil becomes unusable.

(2) Since data of the amount of use of a specific RF coil is supplied to the maker, the maker has many opportunities to sell a new type of RF coil to a user who uses the RF coil with a high frequency. As a result, a diagnosis of a patient as the user can be improved in performance.

[Example 2 of Use of Log File (Counting of the Number of Images Stored)]

In the MRI system 2, it is usual to provide a doctor with an image indicative of test results either in the form of a film or by an electronic method. In the MRI system 2 of the present embodiment, the number of output films of the image indicative of test results can be counted and the electronic size of the image can be measured. The controlling computer 222 counts the number of films or the number and size (e.g., how many megabytes) of electronic files output from the MRI system 2. The electronic size can be measured by the size of an output to an external peripheral device such as an optical disk and a magnetic storage or a PACS (Picture Archiving and Communication System).

The count values are delivered to the communicating computer 21 by the method similar to that in example 1. The maker side can output statistical data on the number of films and the electronic image size that are analyzed by the method similar to that in example 1.

The above results can be provided for the user as a profit and used as materials useful for the sales on the maker side.

(1) The number of films can be prevented from increasing year after year, and an introduction opportunity to reduce management costs can be represented as rational numeric values. For example, a proposal to reduce management costs by making a trial calculation of future total costs from a monthly or annual number of films and introducing an electronic storage such as a PACS can be made to a user of the MRI system 2.

(2) The capacity of an external peripheral device such as an optical disk and a magnetic storage is increasing year after year. A manufacturer can provide a device having a rational capacity that meets the need by knowing the use state on the user side of the MRI system 2. If eight films are used a day in a 640-MB magneto-optical disk drive, its replacement with a 5.2-GB DVD RAM is proposed to a user of the MRI device, thereby reducing the burden on the user in terms of costs for exchange, management, and purchase of media.

4-2 [Example 3 of Use of Log File (Advice on Index of Hospital Management)]

The MRI system 2 outputs the number of images to be picked up a day, the number of patients a day, the imaging time required for each patient, and the like. These throughputs are important factors to hospital management. The unit 20 of the center 1 receives the data from the MRI system 2 through a communication line, compares the data with an average at a national level by executing programs of the unit 20, and supplies the compared data to the maker side. Based on the data, it is possible to determine how much the hospital makes a profit or whether it is significantly high or low. The results of the determination can be provided for the user as profits in the following manner. The management advice is sold to a hospital manager.

(1) There are specialized hospitals having a department of neurosurgery, that of circulatory organs and the like. The characteristics of hospitals are turned out from the amount of use of RF coils and the other investigations. For example, in a hospital with a neurosurgery department, an average of all users as to how long one patient is diagnosed and how many patients are diagnosed a day can be measured and supplied to the maker side. If the throughput of the hospital is significantly lower than the national average obtained after the statistical processing, an advice to improve a routine operation and a sequence can be offered to the hospital manager.

(2) When the foregoing operation or any improvement was performed, it was difficult to know what improvement was caused by the result. The variations in the time required for each patient and the number of patients are statistically measured by the method of the present invention and output from the maker side, thereby objectively proving the advantage of the improvement.

The present invention is not limited to the above embodiment but various modifications can be made. For example, in communication of use-state data, an electronic, magnetic, electromagnetic, or optical medium other than a communication path can be used as a means for supporting an electronic communication line and improving safety. The use of such a medium enables the safety of data to be secured from a malicious intruder into a network. The use state is transmitted to the MRI system center through a normal electronic communication line. In order to download software and pulse sequences from the MRI system center, a CD-ROM or a magneto-optical disk to which they are written is used, or an electronic communication line is used. Authentication is issued from the MRI system center and becomes usable by a hardware medium such as a security card or an authentication number that is provided for the user.

According to the above description, it is the MRI system center 1 that analyzes a log file to calculate the amount of use of hardware and software and then the charge for use thereof. These operations can be carried out by the MRI system 2 and their results can be transmitted to the MRI system center 1.

As described above, the present invention is suitable for spreading and promoting hardware, applications, pulse sequences and clinical protocols in the MRI.

What is claimed is:

1. A magnetic resonance imaging(MRI) system comprising:

a plurality of MRI devices, each said MRI device including a gantry having static and gradient magnetic field generators, at least one radio frequency (RF) coil coupled to an imaging volume, RF transmitter and receiver circuits and controlling computer circuits including a data stare configured to perform MRI procedures in accordance with defined MRI protocol data retrieved from said data store and a communication terminal coupled to a communication network configured to receive and store said MRI protocol data in said data store that is thereafter retrieved and used to perform said MRI procedures which include use of a specified RF coil type, an imaging condition and an MRI pulse sequence to image a selected portion of a body to be imaged;

an MRI system center having a central communication terminal also coupled to said communication network and including:

a unit configured to receive said clinical MRI protocol data describing an MRI procedure from at least one of the plural MRI devices;

a unit configured to store data including the received clinical protocol data, a plurality of MRI clinical protocols being classified with respect to respectively corresponding portions of a body to be imaged, each of the clinical protocols being associated with an RF coil type, an imaging condition and an MRI pulse sequence; and a transmission unit configured to selectively transmit the stored MRI clinical protocol data for a selected portion of a body to be imaged to at least one other of the plural MRI devices where the transmitted MRI clinical protocol data is thereafter used to perform MR imaging processes, wherein data corresponding to an image of a body part acquired using each of plural MRI clinical protocols are stored; and the transmission unit transmits said image data to at least one of the plural MRI devices along with data identifying the respectively corresponding RF coil type, imaging condition and MRI pulse sequence and the image data is displayed by said at least one of the plural MRI devices.

2. The MRI system according to claim 1, wherein the MRI system center further comprises:

a unit configured to receive from said plural MRI devices use-state clinical protocol data; and a unit configured to calculate a use charge for the clinical protocol data based on the use-state data received within a given period of time for an MRI device.

3. The MRI system according to claim 2, wherein the use charge calculate unit calculates a royalty to be credited to an MRI protocol owner as well as the charge for use of MRI protocols.

4. The MRI system of claim 1 wherein the plural MRI devices each comprise:

a display unit configured to display, for each of selected portions of a body to be imaged, a list of the RF coil type, the imaging conditions and the pulse sequence included in a corresponding plurality of clinical protocols; and a receiving unit configured to download, from the MRI system center, at least one data item included in the plurality of clinical protocols and selected from the list.

5. The MRI system according to claim 4, wherein each of the MRI devices further comprises an editing screen forming unit configured to display an editing screen for editing the downloaded data item included in the plurality of clinical protocols.

6. A magnetic resonance imaging (MRI) system comprising:

a plurality of MRI devices, each said MRI device including a gantry having static and gradient magnetic field generators, at least one radio frequency (RF) coil coupled to an imaging volume, RF transmitter and receiver circuits and controlling computer circuits including a data store configured to perform MRI procedures in accordance with defined MRI protocol data retrieved from said data store and a communication terminal coupled to a communication network configured to receive and store said MRI protocol data in said data store that is thereafter retrieved and used to perform said MRI procedures which include use of a specified RF coil type, an imaging condition and an MRI pulse sequence to image a selected portion of a body to be imaged;

an MRI system center having a central communication terminal also coupled to said communication network and including:

a unit configured to receive said clinical MRI protocol data describing an MRI procedure from at least one of the plural MRI devices;

a unit configured to store data including the received clinical protocol data, a plurality of MRI clinical protocols being classified with respect to respectively corresponding portions of a body to be imaged, each of the clinical protocols being associated with an RF coil type, an imaging condition and an MRI pulse sequence;

a transmission unit configured to selectively transmit the stored MRI clinical protocol data for a selected portion of a body to be imaged to at least one other of the plural MRI devices where the transmitted MRI clinical protocol data is thereafter used to perform MR imaging processes, a receiving unit configured to receive, from the plural connected MRI devices, data describing the plurality of clinical protocols;

an image storing unit configured to store data concerning a plurality of sample images corresponding to the stored plurality of clinical protocols; and an image transmission unit configured to transmit the plurality of sample images to the MRI devices and the sample images are displayed by the plural MRI devices.

* * * * *